US012336845B2

(12) United States Patent
Govari

(10) Patent No.: US 12,336,845 B2
(45) Date of Patent: *Jun. 24, 2025

(54) CATHETER WITH PLURALITY OF SENSING ELECTRODES USED AS ABLATION ELECTRODE

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,965

(22) Filed: Mar. 15, 2024

(65) Prior Publication Data

US 2024/0215919 A1    Jul. 4, 2024

Related U.S. Application Data

(63) Continuation of application No. 16/708,285, filed on Dec. 9, 2019, now Pat. No. 11,931,182.

(51) Int. Cl.
*A61B 5/00* (2006.01)
*A61B 5/0538* (2021.01)
(Continued)

(52) U.S. Cl.
CPC .......... *A61B 5/6858* (2013.01); *A61B 5/0538* (2013.01); *A61B 5/068* (2013.01); *A61B 5/6853* (2013.01); *A61B 18/1492* (2013.01); *A61M 25/0074* (2013.01); *A61B 2018/00029* (2013.01); *A61B 2018/0022* (2013.01); *A61B 2018/00375* (2013.01); *A61B 2018/00577* (2013.01); *A61B 2018/00613* (2013.01);
(Continued)

(58) Field of Classification Search
CPC .......... A61B 2018/00214; A61B 2018/00267; A61B 2018/00636; A61B 2018/00708; A61B 2018/00839; A61B 18/124; A61B 18/1405; A61B 5/6868; A61B 5/0538; A61B 5/068; A61B 5/6853
See application file for complete search history.

(56) References Cited

U.S. PATENT DOCUMENTS

| 5,391,199 A | 2/1995 | Ben-Haim |
| 5,496,312 A | 3/1996 | Klicek |

(Continued)

FOREIGN PATENT DOCUMENTS

| JP | H11507574 A | 7/1999 |
| JP | 2007185505 A | 7/2007 |

(Continued)

OTHER PUBLICATIONS

Extended European Sear Reported dated May 19, 2021, from EP Application No. 20212559.7.

(Continued)

*Primary Examiner* — Eun Hwa Kim

(57) ABSTRACT

A system includes a switching assembly and a processor. The switching assembly is connected to multiple electrodes that are disposed on an expandable distal end of a catheter, and is configured to switch the electrodes between a position tracking system, an electrophysiological (EP) sensing module and a generator of an ablative power. The processor is configured to control the switching assembly to switch the electrodes.

20 Claims, 3 Drawing Sheets

(51) Int. Cl.
*A61B 5/06* (2006.01)
*A61B 18/14* (2006.01)
*A61M 25/00* (2006.01)
*A61B 18/00* (2006.01)

(52) U.S. Cl.
CPC .............. *A61B 2018/00791* (2013.01); *A61B 2018/00839* (2013.01); *A61B 2018/00875* (2013.01); *A61B 2018/00958* (2013.01); *A61B 2018/1467* (2013.01); *A61B 2218/003* (2013.01); *A61M 2205/054* (2013.01); *A61M 2205/33* (2013.01); *A61M 2230/65* (2013.01)

(56) References Cited

U.S. PATENT DOCUMENTS

| | | | |
|---|---|---|---|
| 5,562,720 | A | 10/1996 | Stern et al. |
| 5,843,075 | A | 12/1998 | Taylor |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 7,756,576 | B2 | 7/2010 | Levin |
| 7,848,787 | B2 | 12/2010 | Osadchy |
| 7,869,865 | B2 | 1/2011 | Govari et al. |
| 8,456,182 | B2 | 6/2013 | Bar-Tal et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2010/0168548 | A1 | 7/2010 | Govari et al. |
| 2010/0168557 | A1 | 7/2010 | Deno et al. |
| 2010/0191235 | A1 | 7/2010 | Moshe et al. |
| 2016/0128865 | A1 | 5/2016 | Lowe |
| 2017/0042614 | A1 | 2/2017 | Salahieh et al. |
| 2017/0049348 | A1 | 2/2017 | Deno et al. |
| 2018/0235692 | A1 | 8/2018 | Efimov et al. |
| 2019/0008582 | A1 | 1/2019 | Govari et al. |
| 2019/0350649 | A1 | 11/2019 | Sutermeister et al. |
| 2019/0365463 | A1 | 12/2019 | Govari |

FOREIGN PATENT DOCUMENTS

| | | |
|---|---|---|
| JP | 2010220778 A | 10/2010 |
| JP | 2012500657 A | 1/2012 |
| JP | 2016000219 A | 1/2016 |
| JP | 2018519932 A | 7/2018 |
| WO | 9605768 A1 | 2/1996 |
| WO | 2018191149 A1 | 10/2018 |

OTHER PUBLICATIONS

Search Report with English translation dated May 24, 2024, from corresponding Japnese Application No. 2020-203206.

Notice of Reasons for Refusal with English translation dated May 28, 2024, from corresponding Japnese Application No. 2020-203206.

Written Opinion with English translation dated Aug. 22, 2024, from corresponding Japnese Application No. 2020-203206.

Notice of Reasons for Refusal with English translation dated Sep. 10, 2024, from corresponding Japnese Application No. 2020-203206.

Written Opinion with English translation dated Dec. 5, 2024, from corresponding Japnese Application No. 2020-203206.

Decision to Grant a Patent with English translation dated Dec. 24, 2024, from corresponding Japnese Application No. 2020-203206.

CATHETER WITH PLURALITY OF SENSING ELECTRODES USED AS ABLATION ELECTRODE

This application is a continuation of prior filed U.S. patent application Ser. No. 16/708,285 filed on Dec. 9, 2019, which prior application is hereby incorporated by reference as if set forth in full herein.

FIELD OF THE INVENTION

The present invention relates generally to medical probes, and particularly to cardiac multi-electrode electrophysiological (EP) sensing and ablation catheters.

BACKGROUND OF THE INVENTION

Multi electrode catheters for tissue sensing and ablation were previously proposed in the patent literature. For example, U.S. Patent Application Publication 2010/0168548 describes cardiac catheters, including a lasso catheter, for use in a system for electrical mapping of the heart has an array of raised, perforated electrodes, which are in fluid communication with an irrigating lumen. There are position sensors on a distal loop section and on a proximal base section of the catheter. The electrodes are sensing electrodes that may be adapted for pacing or ablation. The raised electrodes securely contact cardiac tissue, forming electrical connections having little resistance.

As another example, U.S. Pat. No. 5,562,720 describes an endometrial ablation device and a method of manufacturing and using the device. An electroconductive expandable member, such as a balloon, is used as a medium for passing RF current through endometrium tissue to heat the endometrium tissue. The power delivered from a power source to the balloon is selectively provided to a plurality of electrode area segments on the balloon with each of the segments having a thermistor associated with it, whereby temperature is monitored and controlled by a feedback arrangement from the thermistors. The selective application of power is provided on the basis of a switching arrangement which provides either monopolar or bipolar energy to the electrodes.

SUMMARY OF THE INVENTION

An embodiment of the present invention provides a system including a switching assembly and a processor. The switching assembly is connected to multiple electrodes that are disposed on an expandable distal end of a catheter, and is configured to switch the electrodes between a position tracking system, an electrophysiological (EP) sensing module and a generator of an ablative power. The processor is configured to control the switching assembly to switch the electrodes.

In some embodiments, the ablative power includes at least one of a radiofrequency (RF) power outputted by an RF generator and irreversible electroporation (IRE) pulses outputted by an IRE pulse generator.

In some embodiments, each of the electrodes includes a plurality of electrode segments.

In an embodiment, when connecting a given electrode to the position tracking system or to the EP sensing module, the switching assembly and the processor are configured to connect each of the electrode segments of the given electrode individually. When connecting the given electrode to the generator of the ablative power, the switching assembly and the processor are configured to jointly connect all the electrode segments of the given electrode.

In another embodiment, the processor is configured to control whether to use the electrode as a position sensor, as an EP sensor, or as an ablation electrode, by evaluating a preset impedance criterion.

In some embodiments, the processor is configured to evaluate the impedance criterion by assessing whether a frequency-dependence of the impedance indicates that the electrode is in contact with blood or with tissue.

There is additionally provided, in accordance with an embodiment of the present invention, a method including, using a switching assembly, interchangeably switching multiple electrodes, which are disposed on an expandable distal end of a catheter, between a position tracking system, an electrophysiological (EP) sensing module and a generator of an ablative power. Using a processor, the switching assembly is controlled to switch the electrodes.

The present invention will be more fully understood from the following detailed description of the embodiments thereof, taken together with the drawings in which:

DETAILED DESCRIPTION OF EMBODIMENTS

Overview

Figure 1:
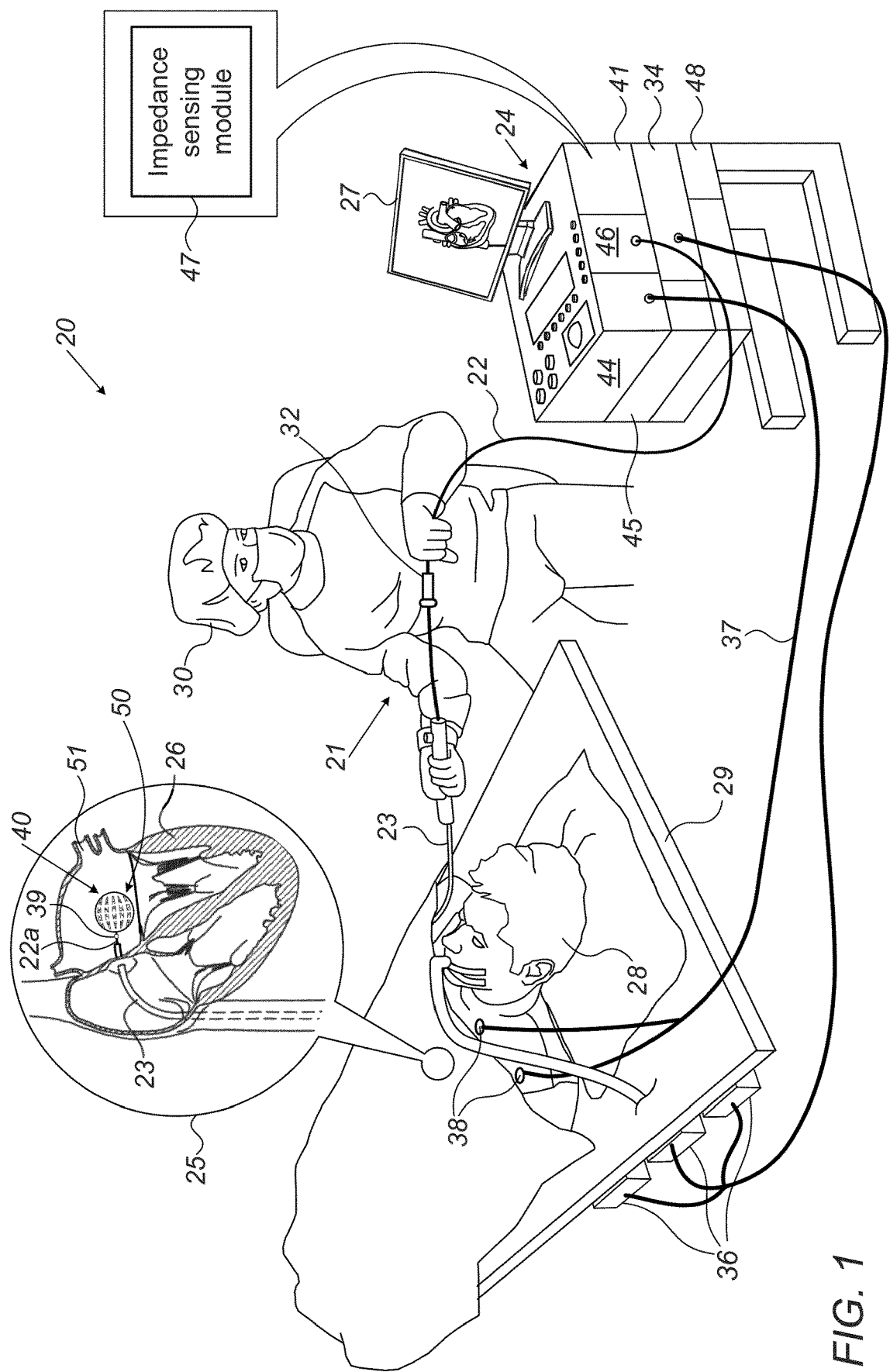
FIG. 1 is a schematic, pictorial illustration of a balloon-catheter based position-tracking, electrophysiological (EP) sensing, and ablation system, in accordance with an embodiment of the present invention.

For efficient sensing and ablation with a medical probe, such as an intra-cardiac radiofrequency (RF) and/or an irreversible electroporation (IRE) catheter with a distal end disposed with multiple electrodes, it is important that (a) the distal end is accurately navigated to a tissue location most suitable for electrophysiological (EP) sensing and ablation, and (b) the electrodes disposed over the distal can effectively acquire EP signals from tissue and/or ablate tissue. For example, when a balloon catheter with multiple electrodes is used for treating cardiac arrhythmia, the balloon has to be brought to a cardiac location, such as an ostium of a pulmonary ventricle (PV), acquire EP signals to verify an arrhythmia, and ablate arrhythmogenic tissue, all using the multiple electrodes.

Similarly, other multi-electrode catheters, such as the Lasso catheter (made by Biosense Webster, Irvine, California) or a basket catheter, also need to have their electrodes capable of such sensing and ablation.

Embodiments of the present invention that are described hereinafter provide techniques to interchangeably use electrodes disposed over the distal end for sensing and for ablation. In some embodiments, the electrodes are initially used as sensors, to track a position of the distal end, so as to navigate it to a cardiac tissue location inside the heart. Subsequently, the electrodes are used for EP sensing. Finally, RF and/or IRE ablation is applied using the electrodes. Typically, the electrodes can be used in a spatially selectable manner, in which at any given time any subset of the electrodes can be switched to be used for any of the above applications. For example, electrodes that have insufficient contact with tissue can be used for position tracking, while others for EP sensing and subsequent ablation.

In the context of the present patent application, the term "applying ablation" covers both applying RF power and applying IRE pulses. Typically, the ablative power comprises either a radiofrequency (RF) power outputted by an RF generator or irreversible electroporation (IRE) pulses outputted by an IRE pulse generator. However, a single generator may be configured to interchangeably output RF power and IRE pulses.

In some embodiments, an expandable multi-electrode catheter (e.g., an inflatable balloon catheter, which is used by way of example hereinafter) is provided that comprises electrodes divided into segments (i.e., into electrode segments). In some embodiments, a balloon catheter is provided with ten electrodes disposed on a membrane of the balloon. Each of the ten electrodes is divided into four segments with one or more temperature sensors, such as thermocouples, located on each electrode segment.

Further provided is a processor-controlled switching box (also referred to as a switching assembly). During navigation of the distal end of a catheter (e.g., a balloon catheter) to a target location for ablation, the disclosed system uses the electrode segments as position sensors of an electrical-impedance-based position tracking sub-system, as described below. Once the balloon is determined to be at the target location (using the position tracking sub-system), the processor controlling the switching box switches an EP sensing module or ablative power to at least part of the electrode segments.

In an embodiment, once catheter is placed in target position, the processor analyzes a characteristic of the measured impedance, such as, for example, the different frequency-dependence of the impedance of blood and tissue, and, using the outcome of the analysis, provides an independent assessment for each electrode segment as to whether the electrode segment is in direct electrical contact with (i.e., touches) cardiac tissue or is not in contact (e.g., the electrode segment is mostly immersed in blood).

The impedance of an electrode can be determined in any of the modes that the electrodes are used in (i.e., position tracking, EP sensing and ablation). Each electrode having a frequency-dependent impedance indicative of tissue is subsequently switched to the EP sensing module or the ablative power source by the processor, using the switching box. An electrode segment with a frequency-dependent impedance indicative of blood is kept as a position sensing electrode by the processor.

In some embodiments, the balloon direction in space is measured using a magnetic sensor on the catheter in vicinity of the balloon, as described below, to further assist a best placement of the balloon against the ostium, e.g., to achieve sufficient electrode contact over an entire circumference of the balloon.

Typically, the processor is programmed in software containing a particular algorithm that enables the processor to conduct each of the processor-related steps and functions outlined above.

By providing electrode segments that are switchable according to navigational tasks, EP sensing tasks, and ablation tasks, the disclosed segmented-electrode sensing and ablation technique can provide safer and more effective diagnostics and treatment. This, in turn, may improve the clinical outcome of, for example, cardiac balloon ablation treatments, such as of PV isolation for treatment of arrhythmia.

System Description

FIG. 1 is a schematic, pictorial illustration of a balloon-catheter based position-tracking, electrophysiological (EP) sensing, and ablation system 20, in accordance with an embodiment of the present invention. System 20 comprises a catheter 21 that is fitted at a distal end 22a of a shaft 22 of the catheter with an RF ablation expandable balloon 40 comprising segmented electrodes 50 (seen in inset 25). In the embodiment described herein, segmented electrodes 50 are used for ablating tissue of an ostium 51 of a PV in a heart 26.

The proximal end of catheter 21 is connected to a control console 24 comprising an ablative power source 45 that can deliver IRE and/or RF power. Console 24 includes a processor 41 that controls a switching box 46 (also referred to as a switching assembly) to switch any segment of a segmented electrode 50 between acting as a position sensing electrode and acting as an ablation electrode. An ablation protocol comprising ablation parameters including impedance criteria is stored in a memory 48 of console 24.

Physician 30 inserts distal end 22a of shaft 22 through a sheath 23 into heart 26 of a patient 28 lying on a table 29. Physician 30 advances the distal end of shaft 22 to a target location in heart 26 by manipulating shaft 22 using a manipulator 32 near the proximal end of the catheter and/or deflection from the sheath 23. During the insertion of distal end 22a, balloon 40 is maintained in a collapsed configuration by sheath 23. By containing balloon 40 in a collapsed configuration, sheath 23 also serves to minimize vascular trauma along the way to target location.

Once distal end 22a of shaft 22 has reached heart 26, physician 30 retracts sheath 23 and partially inflates balloon 40, and further manipulates shaft 22 to navigate balloon 40 to an ostium 51 the pulmonary vein.

In an embodiment, physician 30 navigates the distal end of shaft 22 to the target location by tracking a position of balloon 40 using impedances measured between segmented electrodes 50 and surface electrodes 38.

To perform its functions, processor 41 includes an electrode-impedance-sensing module 47. In the exemplified system, impedance-sensing module 47 receives electrical impedance signals measured between segmented electrodes 50 and surface electrodes 38, which are seen as attached by wires running through a cable 37 to the chest of patient 28. Electrodes 50 are connected by wires running through shaft 22 to processor 41 controlling switching box 46 of interface circuits 44 in a console 24.

A method for tracking the positions of electrodes, such as electrodes 50, using the aforementioned measured impedances is implemented in various medical applications, for example in the CARTO™ system, produced by Biosense-Webster (Irvine, California) and is described in detail in U.S. Pat. Nos. 7,756,576, 7,869,865, 7,848,787, and 8,456,182, whose disclosures are all incorporated herein by reference with a copy provided in the Appendix. This method is sometimes called Advanced Catheter Location (ACL). In an embodiment, console 24 drives a display 27, which shows the tracked position of balloon 40 inside heart 26.

When at target position (e.g., at ostium 51), physician 30 fully inflates balloon 40 and places segmented electrodes 50 disposed over a perimeter of balloon 40 in contact with ostium 51 tissue. Next, physician 30 measures, e.g., using impedance sensing module 47, the impedance of each of segmented electrode segments, as described above. Processor 41 compares the measured impedance of each segment with a preset threshold impedance. If segment impedance is below or equals the preset impedance threshold, which means that the electrode segment is in contact with blood rather than being in good contact with tissue, processor 41 controls switching box 46 to keep the segment operating as a position sensing electrode. If, on the other hand, the segment impedance is above the preset threshold, which means that the electrode segment is in good contact with tissue, the processor controls switching box 46 to operate the segment as an ablation electrode.

As further shown in inset 25, distal end 22a comprises a magnetic position sensor 39 contained within distal end 22a just proximally to expandable balloon 40. During navigation of distal end 22a in heart 26, console 24 receives signals from magnetic sensor 39 in response to magnetic fields from external field generators 36, for example, for the purpose of measuring the direction of ablation balloon 40 in the heart and, optionally, presenting the tracked direction on a display 27, e.g., relative to an orientation of an axis of approximate symmetry of ostium 51. Magnetic field generators 36 are placed at known positions external to patient 28, e.g., below patient table 29. Console 24 also comprises a driver circuit 34, configured to drive magnetic field generators 36.

The method of direction sensing using external magnetic fields is implemented in various medical applications, for example, in the CARTO™ system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference as if set forth in full into this application with a copy provided in the Appendix.

In an embodiment, signals from sensor 39 are further used for position sensing using the aforementioned CARTO™ system.

Processor 41 is typically a general-purpose computer, with suitable front end and interface circuits 44 for receiving signals from catheter 21, as well as for applying RF energy treatment via catheter 21 in a left atrium of heart 26 and for controlling the other components of system 20. Processor 41 typically comprises software in a memory 48 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

While FIG. 1 describes a multi-electrode balloon catheter, the principles of the present technique apply to any catheter having a distal end fitted with multiple electrodes, such as the aforementioned Lasso and basket catheters.

Catheter with Plurality of Sensing Electrodes as Ablation Electrodes

Figure 2:
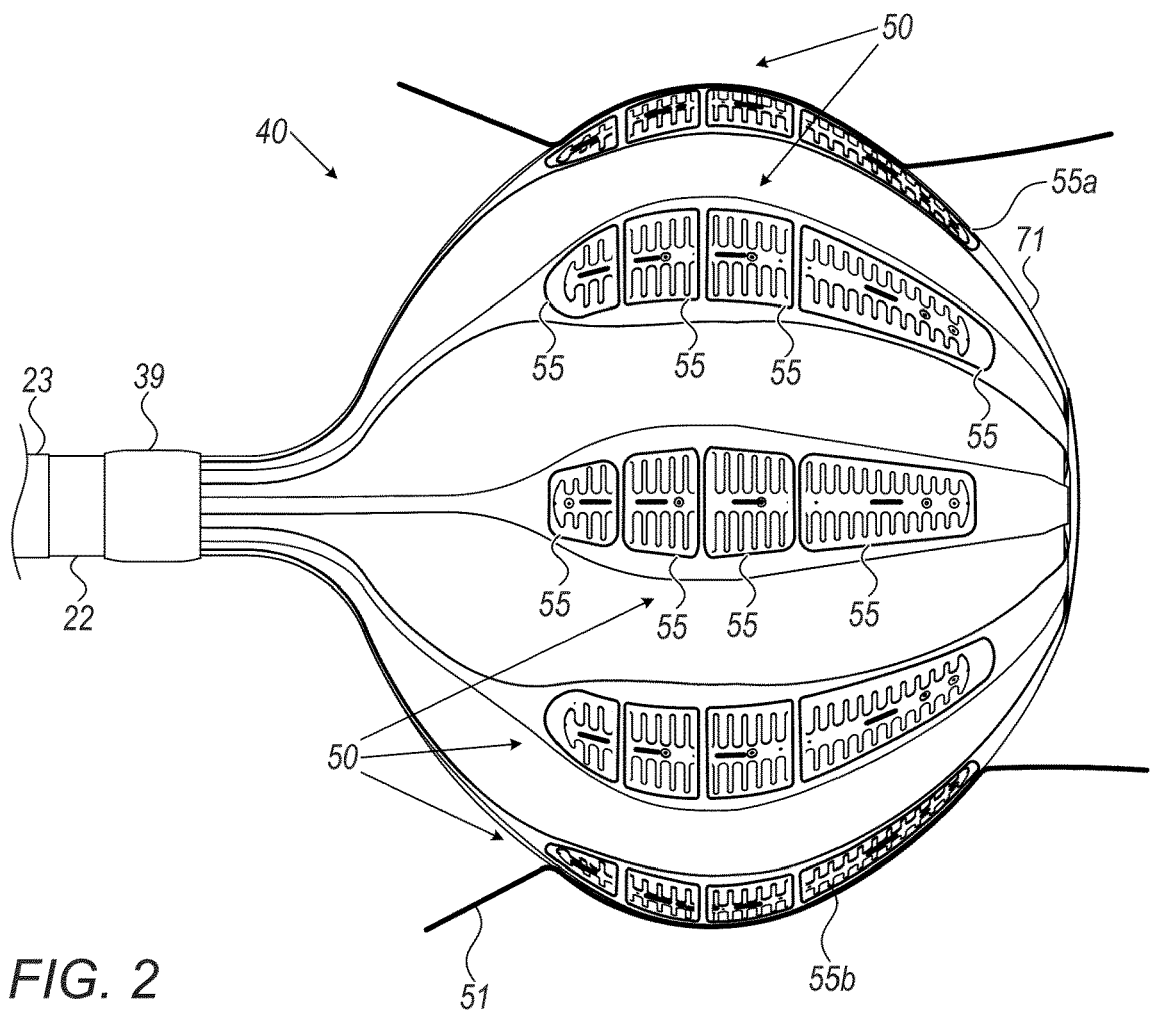
FIG. 2 is a schematic, pictorial side view of a distal end of the balloon catheter of FIG. 1 deployed in a region of a pulmonary vein (PV) and its ostium, in accordance with an embodiment of the invention.

FIG. 2 is a schematic, pictorial side view of the balloon catheter of FIG. 1 deployed in a region of a pulmonary vein (PV) and its ostium 51, in accordance with an embodiment of the invention. The balloon catheter is used to sense EP signals from ostium 51 tissue, to determine an arrhythmia, and to ablate ostium 51 tissue to isolate a source of arrhythmia. Balloon 40 has ten segmented electrodes 50 disposed over a membrane 71 of the balloon. IRE and/or RF power can be delivered from ablative power source 45 independently to each of the four electrode segments 55 of each of the ten electrodes, depending, for example, on the level of physical contact of each segment 55 with tissue during ablation.

As seen in FIG. 2, an electrode segment 55a is not in good contact with tissue. Based on impedance readings from electrode segment 55a as below or equal to the preset impedance value, processor 41 determines the insufficient physical contact of electrode segment 55a. In response, processor 41 controls switching box 46 to maintain electrode segment 55a as a position-sensing electrode.

An electrode segment 55b, on the other hand, is in good contact with tissue. Based on impedance readings from electrode segment 55b as above the preset threshold impedance value, processor 41 determines the sufficient physical contact of electrode segment 55a. In response, processor 41 controls switching box 46 to switch electrode segment 55b to be used as an EP-sensing electrode or as an ablation electrode.

In some embodiments, to determine sufficiency of contact with tissue, the impedance of each electrode segment is monitored by the processor that receives impedance readings sensed by the electrode segment. The processor uses a preset impedance criterion, such as a relation of the impedance readings with respect to a preset threshold impedance, to determine whether a physical contact between any of the electrodes and tissue meets a predefined contact quality with tissue. For example, if the impedance of an electrode segment does not rise above the threshold impedance, the processor determines that the level of contact of the electrode segment with tissue is insufficient (meaning that EP-sensing is of blood signals, or that ablative energy would mainly heat blood). In this case the processor controls the switching box to maintain the electrode segment as a position-sensing electrode. If, on the other hand, an impedance reading from an electrode segment is above the preset threshold impedance (e.g., above a threshold determined by previous experimentation), the processor determines that the contact of the electrode segment with the tissue is good, i.e., meets a predefined contact quality criterion, and that tissue can be either EP sensed, or ablated with the electrode segment. In this case the switching box switches the electrode segment to connect the electrode segment to either an EP sensing module, or the ablative power source.

A technique for sensing electrode-tissue physical contact using analysis of frequency response of tissue is described in U.S. patent application Ser. No. 15/991,291, filed May 29, 2018, entitled "Touch Detection by Different Frequency Response of Tissue," which is assigned to the assignee of the present patent application and whose disclosure is incorporated herein by reference as if set forth in full into this application with a copy in the Appendix. In an embodiment, the processor may use this method to analyze the acquired intra-cardiac signals. However, other techniques to asses level of contact with tissue that utilize electrical measurements provided by segmented electrodes may be used.

The pictorial side view shown in FIG. 2 is chosen by way of example, where other embodiments are possible. For example, in another embodiment, cooling fluid sprays via irrigation holes (not shown) in electrodes 50 to cool ablated tissue. As another example, tissue temperature is measured using temperature sensors (not shown) fitted on electrodes 50.

Figure 3:
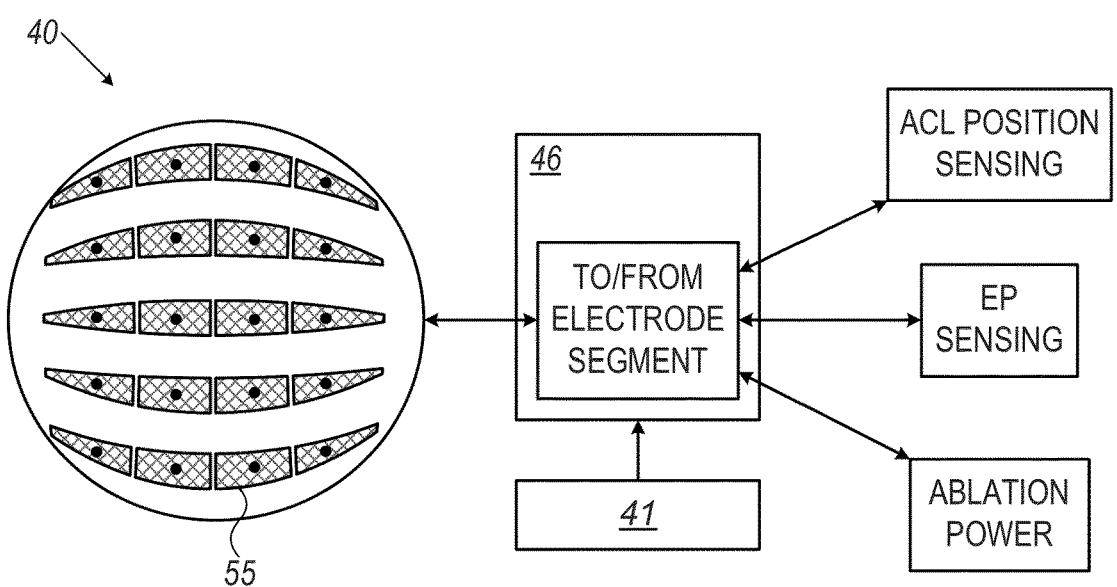
FIG. 3 is a block diagram that schematically describes the functionality of the processor-controlled switching box of FIG. 1, in accordance with an embodiment of the invention.

FIG. 3 is a block diagram that schematically describes the functionality of processor-controlled switching box 46 of FIG. 1, in accordance with an embodiment of the invention. As seen, in response to a command by processor 41, switching box 46 either connects an electrode segment to the aforementioned ACL position-sensing sub-system of system 20 to provide position signals to be used with the ACL position tracking method, or connects the electrode segment to an EP sensing module, or connects the electrode segment to an RF power supply to be used as an ablation electrode.

In another embodiment, when connecting a given electrode to the position tracking system or to the EP sensing module, the switching assembly and the processor are configured to connect each of the electrode segments of the given electrode individually, whereas when connecting the given electrode to the generator of the ablative power, the switching assembly and the processor are configured to jointly connect all the electrode segments of the given electrode.

The block diagram of FIG. 3 is highly simplified to maintain clarity of presentation. Information from other system elements, such as temperature sensors on balloon 40, which do not contribute directly to the clarity presentation, are thus omitted.

Figure 4:
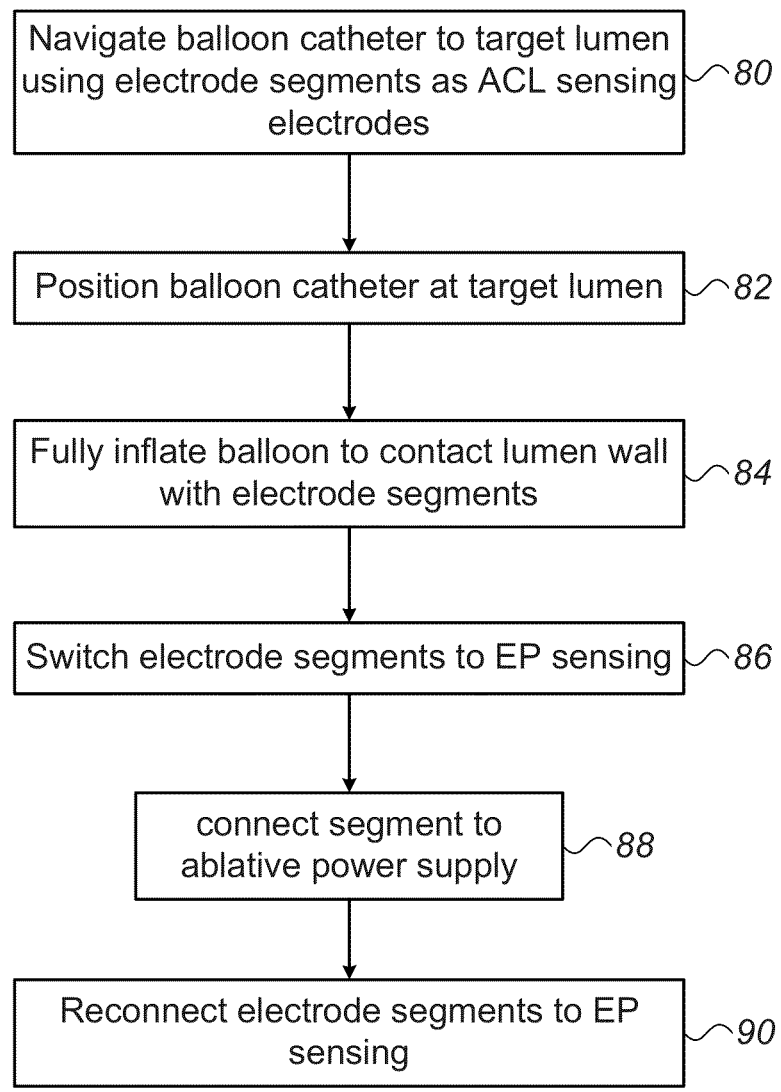
FIG. 4 is a flow chart that schematically illustrates a method for interchangeably using segmented electrodes of the balloon catheter of FIG. 2 for position sensing, electrophysiological (EP) sensing, and ablation, in accordance with an embodiment of the invention.

FIG. 4 is a flow chart that schematically illustrates a method for interchangeably using segmented electrodes of the balloon catheter of FIG. 2 for position sensing, electrophysiological (EP) sensing, and ablation, in accordance with an embodiment of the invention. The algorithm, according to the presented embodiment, carries out a process that begins when physician 30 navigates the balloon catheter to a target location within a lumen of a patient, such as at ostium 51, using electrode segments 55 as ACL-sensing electrodes, at a balloon catheter navigation step 80.

Next, physician 30 positions the balloon catheter at ostium 51, at a balloon catheter positioning step 82. Next, physician 30 fully inflates balloon 40 to contact the lumen wall with electrode segments 55 over an entire circumference of the lumen, at a balloon inflation step 84.

Next, using impedance reading by module 47, the impedance of each of electrode segments 55, typically to one of surface electrodes 38, is measured, and based on an impedance criterion, processor 41 switches part or all electrode segments 55 for use as EP sensing electrodes.

After using the electrodes as EP sensors, to verify an arrythmia, the processor controls switching box 46 to operate the segment as an ablation electrode (e.g., to connect the electrode to ablative power source 45), at a switching step 88. At a switching step 90, physician 30 re-switches part or all electrode segments 55 for use as EP sensing electrodes, to verify arrhythmia was eliminated.

The example flow chart shown in FIG. 4 is chosen purely for the sake of conceptual clarity. In alternative embodiments, additional steps may be performed, such as processor 41 monitoring measured contact force of segments, and acting according to measured contact forces.

While FIG. 4 describes a multi-electrode balloon catheter, the principles of the present technique apply to any catheter having a distal end fitted with multiple electrodes, such as the aforementioned Lasso and basket catheters.

Although the embodiments described herein mainly address pulmonary vein isolation, the methods and systems described herein can also be used in other applications that require a determination of occlusion, such as, for example, in renal denervation, and generally, in ablating other organs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a switching assembly, which is connected to a first electrode and a second electrode, the first electrode and the second electrode each being disposed on an expandable distal end of a catheter, the switching assembly configured to electrically connect the first electrode and the second electrode to one of a positioning system, an electro physiological (EP) sensing module, and a generator of ablative power; and
a processor configured to control the switching assembly to switch the first electrode and the second electrode between the positioning system, the EP sensing module, and the generator of the ablative power,
the processor being configured such that, when a detected impedance is indicative of either the first electrode or the second electrode being in contact with tissue, the processor is configured to cause the switching assembly to (1) switch the electrode in contact with tissue to the generator of ablative power or the EP sensing module and (2) switch the other electrode to the position tracking system.

2. The system according to claim 1, the system being further configured to switch either the first electrode or the second electrode to the position tracking system when a detected impedance at the first electrode or the second electrode is indicative of the electrode being in contact with surrounding blood.

3. The system according to claim 1, the ablative power further comprising at least one of a radiofrequency (RF) power outputted by an RF generator and irreversible electroporation (IRE) pulses outputted by an IRE pulse generator.

4. The system according to claim 1, the first electrode and the second electrode each comprising a plurality of electrode segments.

5. The system according to claim 4, each electrode segment of the plurality of electrode segments comprising a temperature sensor disposed on each segment.

6. The system according to claim 4, the switching assembly and the processor being further configured to:
when connecting either the first electrode or the second electrode to the position tracking system or to the EP sensing module, connect each of the electrode segments of the electrode individually; and
when connecting either the first electrode or the second electrode to the generator of ablative power, jointly connect all the electrode segments of the electrode.

7. The system according to claim 6, the processor being further configured to connect each electrode segment of the electrode to the position tracking system and the EP sensing module simultaneously.

8. The system according to claim 6, the processor being further configured to, in response to determining that a detected impedance at each electrode segment of the plurality of electrode segments is indicative of each electrode segment being in contact with tissue to be ablated, switch each electrode segment of the plurality of electrode segments to the generator of ablative power.

9. The system according to claim 1, the first electrode and the second electrode each comprising at least one temperature sensor disposed on the first electrode and the second electrode.

10. The system according to claim 1, the switching assembly and the processor being further configured to, when the first electrode or the second electrode is connected to one of the position tracking system, the EP sensing module, or the generator of ablative power, actively measure the impedance of the first electrode and the second electrode.

11. A method comprising:
using a switching assembly, interchangeably switching a first electrode and a second electrode, which are disposed on an expandable distal end of a catheter, between a position tracking system, an electrophysiological (EP) sensing module and a generator of ablative power; and
using a processor, controlling the switching assembly to switch the first electrode and the second electrode between the position tracking system, the EP sensing module, and the generator of ablative power;
detecting an impedance of the first electrode or the second electrode; and
switching the first electrode and the second electrode, based on the detected impedance of the first electrode or the second electrode, to one of the position tracking system, the EP sensing module, or the generator of ablative power such that,
when the detected impedance is indicative of either the first electrode or the second electrode being in contact with tissue, the processor is configured to switch the electrode in contact with tissue to the generator of ablative power or the EP sensing module and the other electrode to the position tracking system.

12. The method according to claim 11, wherein applying the ablative power further comprises applying at least one of radiofrequency (RF) ablative power and applying irreversible electroporation (IRE) pulses.

13. The method according to claim 11, the first electrode and the second electrode each comprising a plurality of electrode segments.

14. The method according to claim 13, each electrode segment of the plurality of electrode segments comprising a temperature sensor disposed on each segment.

15. The method according to claim 13, the switching assembly and the processor being further configured to:
when connecting either the first electrode or the second electrode to the position tracking system or to the EP sensing module, connect each electrode segment of the electrode individually; and
when connecting either the first electrode or the second electrode to the generator of ablative power, jointly connect all electrode segments of the electrode.

16. The method according to claim 15, the processor being further configured to connect each electrode segment of the electrode to the position tracking system and the EP sensing module simultaneously.

17. The method according to claim 15, the processor being further configured to, in response to determining that a detected impedance at each electrode segment of the plurality of electrode segments is indicative of each electrode segment being in contact with tissue, switch each electrode segment of the plurality of electrode segments to the generator of ablative power.

18. The method according to claim 13, the first electrode and the second electrode each comprising a temperature sensor disposed on the first electrode and the second electrode.

19. The method according to claim 11, the switching assembly and the processor being further configured to, when a detected impedance is indicative of both the first electrode and the second electrode being in contact with tissue, switch both the first electrode and the second electrode to the generator of ablative power or the EP sensing module.

20. The method according to claim 11, the switching assembly and the processor being further configured to, when the first electrode or the second electrode is connected to one of the position tracking system, the EP sensing module, or the generator of ablative, actively measure the impedance of the first electrode and the second electrode.

* * * * *